United States Patent [19]

Hachmann et al.

[11] Patent Number: 5,190,724
[45] Date of Patent: Mar. 2, 1993

[54] PROCESS FOR DISINFECTING MEDICAL MOLDING MATERIALS

[75] Inventors: Klaus Hachmann, Hilden; Klaus Bansemir, Langenfeld; Karlheinz Disch, Haan, all of Fed. Rep. of Germany

[73] Assignees: Henkel Kommanditgesellschaft auf Aktien, Duesseldorf; ESPE Stiftung & Co. Produktions-und Vertriebs KG, Seefeld, both of Fed. Rep. of Germany

[21] Appl. No.: 663,818

[22] PCT Filed: Sep. 11, 1989

[86] PCT No.: PCT/EP89/01052
§ 371 Date: May 17, 1991
§ 102(e) Date: May 17, 1991

[87] PCT Pub. No.: WO90/03191
PCT Pub. Date: Apr. 5, 1990

[30] Foreign Application Priority Data
Sep. 19, 1988 [DE] Fed. Rep. of Germany ....... 3831779
Dec. 27, 1988 [DE] Fed. Rep. of Germany ....... 3844024

[51] Int. Cl.⁵ .............................................. A61L 2/18
[52] U.S. Cl. ...................................... 422/28; 422/36; 134/42

[58] Field of Search ................. 422/28, 36; 134/42; 106/38.51, 38

[56] References Cited

U.S. PATENT DOCUMENTS 3,709,866  1/1973  Waller ............................ 106/38.51
3,912,450  10/1975 Boucher .......................... 422/20
3,983,252  9/1976  Buchalter ........................ 422/36
4,836,853  6/1989  Gribi ............................. 106/35

OTHER PUBLICATIONS

Chemical Abstracts, vol. 109, Nr. 8, Aug. 22, 1988, J. Viohl et al.; "Dimensional Stability of alginate Impressions".
Seymour Block, Disinfection, Sterilization, and Preservation, 1983, pp. 67–70, 227, 484, 485.

Primary Examiner—Robert J. Warden
Assistant Examiner—Laura E. Collins
Attorney, Agent, or Firm—Ernest G. Szoke; Wayne C. Jaeschke; Norvell E. Wisdom, Jr.

[57] ABSTRACT

In the process disclosed, medical molding materials are treated with an aqueous solution of a disinfectant which contains, in addition, 0.1 to 15 wt.% of a soluble alcohol. This ensures high dimensional stability and good surface quality of the mold, even in the case of critical molding materials as alginates.

20 Claims, No Drawings

PROCESS FOR DISINFECTING MEDICAL MOLDING MATERIALS

BACKGROUND OF THE INVENTION

1. Field of the Invention

This invention relates to processes for disinfecting medical molding materials and molded articles made from them.

2. Statement of Related Art

In many fields of medicine, true-to-size models of organs or parts of organs have to be made on a more or less frequent basis. Thus, in pathology and in surgery, models are needed for demonstration or documentation purposes; in orthopedics, models are used for the fitting of prostheses while, in dentistry, false teeth are made from models. To make the model, a three dimensional negative of the organ in question is first prepared using molding materials and is then used as a mold for making the actual model, optionally after storage. Many materials are used to produce the negative, all of which have the property of being plastically deformable at first and then hardening after a short time to form a more or less elastic mass. Molding is carried out by pressing the organ in question into the plastic molding material and leaving it therein until the mass has hardened. The model itself is made by casting, for example by introducing mixtures of water and plaster of Paris into the negative mold.

In dentistry, there are rigid and elastic molding materials. Whereas rigid molding materials, such as plaster of Paris, zinc oxide/eugenol pastes, waxes and guttapercha are mainly used to determine the position of teeth to one another, i.e. to record bites, elastic molding materials based on synthetic or natural polymers which harden through physical or chemical crosslinking reactions are mainly used for making dental models.

At present, the most important synthetic polymers for this purpose are silicones, polyethers and polysulfides which are all chemically crosslinked. In the case of silicones, a basic distinction is drawn between condensation-crosslinking materials (these materials are hardened with organic tin or titanium compounds as catalysts which crosslink the starting polysiloxanes after the removal of terminal groups) and so-called addition-crosslinking silicone molding materials which are hardened by reaction of a vinyl-terminated polysiloxane with a polysiloxane containing SiH groups in the presence of certain platinum catalysts. In addition to polysulfides, polyether materials are also very important by virtue of their hydrophilic properties because the effective wetting, for which these properties provide, enables the tooth situation in the mouth to be particularly well reproduced, even in aqueous medium. In this case, the crosslinking reaction is based on the polymerization of epimine-terminated polyether prepolymers initiated by sulfonium salt catalysts.

The most important natural polymers are polymeric carbohydrates among which the alginates have the greatest significance. With these materials, aqueous elastic gels, which are less stable than the synthetic materials, are formed during the solidification reaction.

It is known that alginate molding materials can provide sufficiently accurate jaw impressions and are widely used because they are inexpensive to produce. This molding material is supplied to the user in the form of an alginate-containing powder which is mixed with a defined quantity of water before use. During mixing, the reactants alginic acid salt and calcium salt pass into solution, react with one another and form an insoluble, elastic hydrogel. In addition to a soluble alginic acid salt, such as potassium or sodium alginate, and a moderately soluble calcium salt, such as calcium sulfate, retarders, such as sodium phosphate or sodium pyrophosphate, fillers, such as kieselguhr, and complex transition metal fluorides, such as potassium hexafluorotitanate, are generally used. It is also of advantage to use small quantities of pyrogenic silica to obtain thixotropic behavior. To prevent dust emission from this alginate powder mixture, the mixture may be granulated by addition of soluble and insoluble organic compounds (cf. for example EP-A 0 058 203 and also DE-A 34 39 884 and DE-A 34 10 923).

The compositions of the alginate molding materials may vary within relatively wide limits. Thus, they may contain from 10 to 30% by weight sodium or potassium alginate, from 10 to 30% by weight calcium sulfate, from 0.5 to 5% by weight sodium phosphate and/or sodium pyrophosphate and, for the rest, typical fillers, flavorings and thixotropic auxiliaries. Particularly suitable fillers are kieselguhrs, sodium or potassium hexafluorotitanate and also zinc oxides.

In contrast to the alginates, molding materials based on agar-agar are reversible materials (so-called hydrocoloids) which, in principle, may be repeatedly reused. For molding, the highly aqueous agar-agar gel is converted in a water bath into the sol state, the molding material is introduced into the mouth by spoon and is converted back into a firm elastic state (gel) by the addition of cold water by spoon.

In practice, the negative mold and the actual model are generally not made by the same person. Instead, the negative mold after removal from the original is transported over more or less long distances to a model workshop where the model is made by specially trained personnel. As a result of the production process, the negative mold can be undesirably contaminated with germs, among which pathogenic germs cannot be ruled out. A particular danger in this regard in dental medicine is contamination with hepatitis viruses. Accordingly, it was proposed some time ago to disinfect the negative mold before it is passed on to eliminate any risk to people subsequently coming into contact with the mold.

However, known surface and medical instrument disinfectants could not be satisfactorily used for molding materials. The difficulties lay in the fact that a generally different spectrum of germs had to be controlled on a totally different surface, the disinfection process was not adversely to affect either the dimensional stability or the surface quality of the molding materials and the moldability of the actual model had to remain guaranteed. In the particular case of the hydrophilic materials, such as polyethers, alginates, hydrocolloids and hydrophilic silicones, exposure of the molded material to aqueous disinfectants and also alcoholic disinfectants greatly affected the quality of the model subsequently made. To overcome these difficulties, it was proposed as an alternative, for example, to add an antimicrobial agent to the molding material before molding in order thus to rule out subsequent effects on the mold (G. Lott, H. K. Gribi, Quintessence International, Vol. 19, No. 8, 571 (1981); see also EP 265 776 and DD 244 068). However, even this process does not solve all problems because many basically effective disinfectants do not develop their full effectiveness in this particular application or are incompatible with the molding material or the oral mucous membrane. In addition, contamination of the spoon in which the mold is situated is not eliminated.

DESCRIPTION OF THE INVENTION

The problem addressed by the present invention in this regard is to provide a suitable process for the subsequent disinfection of the molded material. This problem is solved by the use of disinfectants in dilute aqueous-alcoholic solution.

Accordingly, the present invention relates to a process for the disinfection of medical molding materials in which, after solidification and removal from the original, the molding materials are contacted with an aqueous solution of a disinfectant, characterized in that this solution contains from 0.1 to 15% by weight of a soluble alcohol.

The new process not only achieves rapid and thorough destruction of all relevant germs and viruses, it also reduces adverse influences on the dimensional stability, surface quality and detail reproduction of the negative to such an extent that they are no longer troublesome in practice. The same also applies to polyethers and hydrophilic silicones and even to the extremely sensitive polymeric carbohydrates, particularly the alginates, which are widely used as molding materials in dental medicine.

The process is generally carried out by immersing the negative immediately after removal from the organ to be reproduced or, preferably, after brief rinsing with water into a prepared solution of the disinfectant to such an extent that all possibly contaminated surfaces are wetted by the solution. The solution is generally at room temperature although, providing the molding material allows, disinfection may even be carried out at elevated temperatures. The contact times are governed by the required degree of disinfection and, at room temperature, are generally between 1 and 20 minutes, preferably between 1 and 10 minutes and more preferably between 1 and 5 minutes. The mold is then removed, generally rinsed once more with water and suitably stored pending subsequent use. However, disinfection need not necessarily be carried out after production of the negative mold and, instead, may even be carried out at a later stage, optionally in addition to a disinfection treatment immediately after production. Instead of the preferred immersion, the mold may also be sprayed with the active-substance solution for disinfection.

The alcohols to be used in accordance with the invention should be soluble in water in the particular in-use concentration. Suitable alcohols are, for example, butanediol, butanol, triethylene glycol, polyethylene glycols and mixed polyethylene/polypropylene glycols.

The alcohols are preferably infinitely miscible with water. Accordingly, $C_{1-3}$ alcohols and $C_{3-6}$ ether alcohols are preferably used. Examples of $C_{1-3}$ alcohols are ethanol, isopropanol, n-propanol, 1,2-propylene glycol and glycerol. Examples of $C_{3-6}$ ether alcohols are diethylene glycol, triethylene glycol and butyl glycol. Aldehydes of the same C chain length predominantly present as hydrates in aqueous solution, for example glyoxal, have the same effect and may therefore completely or partly replace the alcohols. Accordingly, they are regarded as alcohols in the context of the present invention. Ethanol, n-propanol and glyoxal are particularly preferred.

The addition of the alcohols to the aqueous disinfectant solutions surprisingly has far less of an adverse effect on dimensional accuracy and surface quality during disinfection of the negative mold than purely aqueous solutions or predominantly alcoholic solutions of the disinfectants. The concentration of alcohol is generally between about 0.1 and 15% by weight and preferably between 1 and 10% by weight, based on the weight of the final disinfection solution. The most suitable concentration depends upon the type of alcohol used and is approximately 1% by weight in the case of isopropanol for example, between about 2 and 5% by weight in the case of n-propanol and glycerol, between 1 and 3% by weight in the case of 1,2-propylene glycol and between about 2 and 6% by weight in the case of ethanol.

Although some of the alcohols to be used in accordance with the invention also have a certain antimicrobial effect and, in the case of glyoxal or formaldehyde, even a strong antimicrobial effect, the disinfection solutions additionally contain typical disinfecting agents. The choice of disinfectant agents and the concentrations in which they are used is determined primarily by the germ spectrum to be controlled and also by the intended disinfection time. In principle, suitable broad-spectrum disinfecting agents are, for example, aldehyde, phenols, quaternary ammonium compounds, biguanides, active halogen compounds and peroxidic compounds, which may be used either individually or in suitable combinations. Examples of suitable disinfecting agents from these classes are glutaraldehyde, o-phenylphenol, p-chloro-n-cresol, didecyl dimethyl ammonium chloride, benzyl dimethyl alkyl ammonium chloride, oligohexamethylenebiguanide hydrochloride, hydrogen peroxide and peracetic acid. It may even be appropriate to add one or more narrow-spectrum agents, for example fungicides, such as for example undecylenic acid derivatives. Particularly preferred disinfecting agents for the process according to the invention are aldehydes, particularly succindialdehyde and glutardialdehyde, and peroxidic compounds.

Concentrations of from 0.1 to 10% by weight and preferably from 0.5 to 7% by weight of disinfecting agent are sufficient for most cases, although it is readily possible in special cases to exceed these limits. Where the disinfection solutions contain both glutardialdehyde and glyoxal—a preferred embodiment of the invention— these aldehydes are preferably used in a ratio by weight of from 2:1 to 1:10 and more preferably in a ratio by weight of from 2:1 to 1:5. The disinfection solution contains the two aldehydes preferably in a quantity of 0.5 to 7% by weight and more preferably in a quantity of 1 to 5% by weight, expressed as the sum of both aldehydes. Up to 3% by weight and preferably from 0.01 to 2% by weight of other disinfecting agents may also be present although, in special cases, there may even no need to add other disinfecting agents.

In addition to the disinfecting agents, the disinfection solutions may contain other typical auxiliaries, including above all surfactants which are intended to facilitate wetting of the negative mold. Nonionic and, preferably, anionic surfactants are primarily used, although other types of surfactant may also be used providing they are sufficiently compatible with the materials to be disinfected. (Nonionic surfactants, i.e. generally adducts of ethylene oxide and long-chain alcohols or phenols, are not regarded as alcohols in the context of the invention.) In addition, the disinfection solutions may contain pH regulators and buffers for safely adjusting the preferred pH value of the solution of 2 to 11 and preferably 3 to 9. Suitable other auxiliaries are sequestering agents, perfumes, dyes, foam inhibitors and hydrotropes and also additives which make the negative mold easier to reproduce with plaster of Paris, such as for example inorganic fluorides, for example $Na_2TiF_6$. The quantity of auxiliaries in the disinfection solution is preferably between 0.01 and 10% by weight and more preferably between 0.1 and 5% by weight. The quantity of surfactants preferably makes up from 0 to about 1% by weight, more preferably from 0 to 0.5% by weight and most preferably from 0.01 to 0.3% by weight of the solution.

The disinfection solutions may be prepared from the individual components immediately before application of the process, although it is more convenient and safer to use already prepared solutions or merely to dilute corresponding concentrates.

A particularly suitable disinfection solution for the process according to the invention has the following composition:

| | |
|---|---|
| 0.5 to 5% by weight | glyoxal |
| 0 to 10% by weight | alcohol from the group consisting of ethanol, n-propanol and mixtures thereof, |
| 0.5 to 10% by weight | aldehyde from the group consisting of succindialdehyde, glutardialdehyde and mixtures thereof, |
| 0 to 3% by weight | one or more other disinfecting agents, |
| 0 to 10% by weight | one or more auxiliaries from the group consisting of surfactants, pH regulators, sequestering agents, perfumes, dyes, foam inhibitors, hydrotropes and inorganic fluorides and |
| balance to 100% by weight | water. |

The process according to the invention is preferably used for the disinfection of molding materials in dental and jaw medicine. However, the process is by no means limited to this particular field of application and, instead, may be widely used not least by virtue of the high material compatibility. In no case was the addition of the alcohols found to restrict the suitability of the preparations for other disinfection measures.

EXAMPLES

1. Disinfection solutions

The aqueous solutions used for the following tests had the following composition (in % by weight, balance water):

| | A | B | C | D |
|---|---|---|---|---|
| Glyoxal | 0.88 | 1.76 | 0.88 | 0.88 |
| Glutaraldehyde | 0.45 | 0.90 | 0.45 | 0.45 |
| Ethanol | 5.0 | 5.5 | — | — |
| n-Propanol | — | — | 3.5 | — |
| Glycerol | — | — | — | 4.0 |
| Alkylbenzenesulfonate | 0.40 | 0.80 | 0.40 | 0.40 |
| Nonionic surfactant (EO adduct) | 0.20 | 0.40 | 0.20 | 0.20 |
| Other auxiliaries (sequestering agents, hydrotrope, dye) | 0.21 | 0.42 | 0.21 | 0.21 |

2. Material compatibility

This test was carried out on alginate-based molding materials which, of all the molding materials used today in dentistry, react the most sensitively to mishandling. The test material used was Palgat, a product of the Espe company of Seefeld, Federal Republic of Germany. The test was carried out as follows:

20 g of the alginate were thoroughly mixed with 40 ml distilled water and the resulting mixture cast into the sample mold ("apparatus for detail reproduction" according to ADA Specification No. 19 (American Dental Association), J. Am. Dent. Assoc., Vol. 84, April 1977, pages 733 et seq). Excess alginate was displaced by a smooth glass plate. After hardening for 15 minutes at room temperature (23°±1° C.) in a Hygrophor (100% relative air humidity), the mold was removed and immediately placed in the disinfection bath containing solutions A, B, C and D. After the residence times in the disinfection bath (temperature 23°±1° C.) shown in the Table, the mold was rinsed in a gentle stream of tap water for 10 seconds. The mold was then cast with plaster of Paris (Moldano, a product of Bayer AG, Leverkusen, Federal Republic of Germany). In order completely to harden the plaster cast, the model and negative mold were stored for 30 minutes in a Hygrophor (23°±1° C., 100% relative air humidity). The alginate mold was then carefully separated from the plaster and the plaster cast carefully examined under a microscope for dimensional changes and for surface quality.

The results are shown in Table 1 below for various contact times of the disinfection solution. The figures represent perecent for the dimensional changes and an evaluation index of 1 to 3 (no significant influences; slight influence with no effect on precision; strong unacceptable influences) for the surface quality of the plaster cast.

TABLE 1

| | Surface quality | | | | | | Dimensional change | | |
|---|---|---|---|---|---|---|---|---|---|
| | Alginate | | | Gypsum | | | | | |
| | (after minutes) | | | | | | (after minutes) | | |
| Solution | 5 | 10 | 20 | 5 | 10 | 20 | 5 | 10 | 20 |
| A | 1 | 1 | 1 | 1-2 | 2 | 2 | −0.33 | −0.15 | −0.13 |
| B | 1 | 1 | 1 | 2 | 2 | 2 | −0.02 | −0.54 | −0.52 |
| C | 1 | 1 | 1 | 2 | 2 | 2 | +0.03 | −0.06 | −0.28 |
| D | 1 | 1 | nd | 1-2 | 1-2 | 3 | +0.28 | +0.06 | nd |

The figures show that, even after contact times of 10 to 20 minutes, neither surface quality nor dimensional accuracy had undergone changes which could impair the quality of the prosthetic work except for solution D after 20 minutes.

3. Disinfection effect

To test the disinfection effect, alginate molding material was prepared by stirring water and Palgat (a product of the Espe company of Seefeld, Federal Republic of Germany) in a rubber beaker in accordance with the manufacturer's instructions and then processed to lenticular test specimens approx. 22 mm in diameter and 5 mm thick by spreading onto a spotting plate of porcelain (hardening time 5 minutes). The test specimens were then contaminated by introduction into a germ suspension containing more than $10^8$ germ-forming units of Staphylococcus aureus per milliliter.

After contamination, the germ carriers were placed in open Petri dishes, stored over water for 30 minutes in an exsiccator and, for disinfection, were then introduced into the disinfection solution for a certain time (5 or 10 minutes) to ensure thorough wetting. To count the germs still surviving, the germ carriers were then individually shaken with 10 g glass beads in 20 ml of an inactivation solution for 2 minutes, the numbers of germs in the solution then being determined in the usual way by inoculation onto agar and incubation.

The results are shown in Table II below, the factors of the reduction in germ count being shown in logarithmic form in relation to treatment with water alone (as standard). The individual figures are each averages of 6 individual determinations.

TABLE II

| Solution of | Reduction factor (log) after | |
|---|---|---|
| Example | 5 minutes | 10 minutes |
| 1A | 5.1 | 5.2 |
| 1B | 5.5 | 5.5 |
| 1C | 4.9 | 5.3 |
| 1D | 5.5 | 5.1 |

The results show that, in every case, the moldings were safely disinfected.

What is claimed is:

1. In a process for the disinfection of medical molding materials in which, after hardening and removal from the original, the molding materials are contacted with an aqueous solution, said aqueous solution contains a disinfectant selected from the group consisting of aldehydes, phenols, quaternary ammonium compounds, biguanides, active halogen compounds, and peroxidic compounds, wherein the improvement comprises the presence in the aqueous solution of 0.1 to 15% by weight of material selected from the group consisting of soluble alcohols and mixtures thereof.

2. A process as claimed in claim 1 in which the aqueous solution comprises material selected from the group consisting of $C_{1-3}$ alcohols, $C_{3-6}$ ether alcohols, and mixtures of such alcohols.

3. A process as claimed in claim 2 in which the aqueous solution comprises material selected from the group consisting of ethanol, n-propanol, and glyoxal.

4. A process as claimed in claim 1 in which the aqueous solution comprises from 1 to 10% by weight of water soluble alcohols and mixtures thereof.

5. A process as claimed in claim 1 in which the aqueous solution comprises from 0.1 to 10% by weight of disinfecting agent.

6. A process as claimed in claim 5 in which the aqueous solution contains from 0.1 to 10% by weight of disinfecting agent selected from the group consisting of succindialdehyde, glutardialdehyde, and peroxidic compounds.

7. A process as claimed in claim 3 in which the aqueous solution comprises a combination of glutardialdehyde and glyoxal in a ratio by weight of from 2:1 to 1:10.

8. A process as claimed in claim 1 in which the medical molding materials are alginate molding materials.

9. A process as claimed in claim 7, in which the aqueous solution comprises a combination of glutardialdehyde and glyoxal in a ratio by weight of from 2:1 to 1:5.

10. A process as claimed in claim 9 in which the aqueous solution comprises from 0.5 to 7% by weight of disinfecting agent.

11. A process as claimed in claim 5 in which the aqueous solution comprises from 0.5 to 7% by weight of disinfecting agent.

12. A process as claimed in claim 11 in which the medical molding materials are alginate molding materials.

13. A process as claimed in claim 10 in which the medical molding materials are alginate molding materials.

14. A process as claimed in claim 9 in which the medical molding materials are alginate molding materials.

15. A process as claimed in claim 7 in which the medical molding materials are alginate molding materials.

16. A process as claimed in claim 6 in which the medical molding materials are alginate molding materials.

17. A process as claimed in claim 5 in which the medical molding materials are alginate molding materials.

18. A process as claimed in claim 4 in which the medical molding materials are alginate molding materials.

19. A process as claimed in claim 3 in which the medical molding materials are alginate molding materials.

20. A process as claimed in claim 2 in which the medical molding materials are alginate molding materials.

* * * * *

UNITED STATES PATENT AND TRADEMARK OFFICE
CERTIFICATE OF CORRECTION

PATENT NO. : 5,190,724
DATED : March 2, 1993
INVENTOR(S) : Hachmann, et. al.

It is certified that error appears in the above-indentified patent and that said Letters Patent is hereby corrected as shown below:

On the Title page, item [75], inventors should read:
--Klaus Hachmann, Hilden; Klaus Bansemir, Langenfeld;
 Karlheinz Disch, Haan; Walter Dasch, Muenchen; Reinhard
 Pichl,Hechendorf; Klaus Ellrich,Woerthsee, all of Fed. Rep.
 of Germany.

Signed and Sealed this

Eleventh Day of January, 1994

*Attest:*

BRUCE LEHMAN

*Attesting Officer*     *Commissioner of Patents and Trademarks*